United States Patent
Tian et al.

(10) Patent No.: US 10,130,702 B2
(45) Date of Patent: Nov. 20, 2018

(54) VACCINE COMPOSITION AND PREPARATION METHOD AND USE THEREOF

(71) Applicant: PULIKE BIOLOGICAL ENGINEERING, INC., Luoyang (CN)

(72) Inventors: Kegong Tian, Luoyang (CN); Wenqiang Pang, Luoyang (CN); Jinzhong Sun, Luoyang (CN); Xuke Zhang, Luoyang (CN)

(73) Assignee: PULIKE BIOLOGICAL ENGINEERING, INC., Luoyang (CN)

( * ) Notice: Subject to any disclaimer, the term of this patent is extended or adjusted under 35 U.S.C. 154(b) by 0 days.

(21) Appl. No.: 15/885,267

(22) Filed: Jan. 31, 2018

(65) Prior Publication Data
US 2018/0161424 A1 Jun. 14, 2018

Related U.S. Application Data

(63) Continuation of application No. PCT/CN2017/109357, filed on Nov. 3, 2017.

(30) Foreign Application Priority Data

Dec. 1, 2016 (CN) .......................... 2016 1 1091770

(51) Int. Cl.
| | | |
|---|---|---|
| *A61K 39/235* | (2006.01) | |
| *A61K 39/39* | (2006.01) | |
| *A61K 39/17* | (2006.01) | |
| *A61K 39/145* | (2006.01) | |
| *A61K 39/215* | (2006.01) | |
| *A61P 31/20* | (2006.01) | |
| *A61K 39/00* | (2006.01) | |

(52) U.S. Cl.
CPC .......... *A61K 39/235* (2013.01); *A61K 39/145* (2013.01); *A61K 39/17* (2013.01); *A61K 39/215* (2013.01); *A61K 39/39* (2013.01); *A61P 31/20* (2018.01); *A61K 2039/552* (2013.01); *A61K 2039/70* (2013.01)

(58) Field of Classification Search
CPC ...... A61K 39/235; A61K 39/39; A61K 39/17; A61K 39/215; A61K 39/145; A61P 31/20
See application file for complete search history.

(56) References Cited

U.S. PATENT DOCUMENTS

2005/0266019 A1* 12/2005 Rodenberg ............. A61K 39/12
424/199.1

FOREIGN PATENT DOCUMENTS

| WO | 2015024932 A1 | 2/2015 |
| WO | WO 2016/020885 | * 2/2016 |

OTHER PUBLICATIONS

Derwent abstract of Bai et al. CN103789272A; May 2014.*
Cheng et al. (Journal of Vaccines and Immunology. 2016; 2 (1): 019-022).*
Jin et al. (Derwent abstract of CN101607083; Dec. 2003).*
Li et al. "Comparison of Nd—Al Recombined Vaccine and Nd-IB-EDS Triple Vaccine Using Different Types of Adjuvant." China Poultry 8 (2010): 008).*
Sequence alignment of SEQ ID No. 2 with GenEmbl db access No. FR872912 by Marek et al. 2012.*
Search Report for Related PCT Application No. PCT/CN2017/109357, dated Feb. 5, 2018, 13 pages.
Schachner et al., "Recombinant FAdV-4 fiber-2 protein protects chickens against hepatitis-hydropericardium syndrome (HHS)", Article in Vaccine 32(9)—Jan. 2014, pp. 1086-1092.
Zhou et al., "Recent development in vaccine adjuvant research", Chinese Journal of New Drugs 2013, 22(1), pp. 34-42, English Abstract Included.

* cited by examiner

*Primary Examiner* — Shanon A. Foley
(74) *Attorney, Agent, or Firm* — Ditthavong & Steiner, P.C.

(57) ABSTRACT

The present disclosurerelates to a vaccine composition, wherein the vaccine composition comprises an immune amount of fowl adenovirus Fiber-2 protein or an immune amount of a live vector recombined with gene of the fowl adenovirus Fiber-2 protein, and a pharmaceutically acceptable carrier. The vaccine composition can provide effective immune protection against different serotypes of adenoviruses and provide a protection rate of 100% at low levels of immunogenic components, showing good immunological efficacy.

15 Claims, No Drawings

Specification includes a Sequence Listing.

SEQUENCE LISTING

```
<160> NUMBER OF SEQ ID NOS: 8

<210> SEQ ID NO 1
<211> LENGTH: 1440
<212> TYPE: DNA
<213> ORGANISM: Fowl adenovirus

<400> SEQUENCE: 1
atgctgcgtg ctccgaaacg tcgtcactct gaaaacggtc agccggaaac tgaagctggt      60
ccgtctccgg ctccgatcaa acgtgctaaa cgtatggttc gtgcttctca gctggacctg     120
gtttacccgt tcgactacgt tgctgacccg gttggtggtc tgaacccgcc gttcctgggt     180
ggttctggtc cgctggttga ccagggtggt cagctgaccc tgaacgttac cgacccgatc     240
atcatcaaaa accgttctgt tgacctggct cacgacccgt ctctggacgt taacgctcag     300
ggtcagctgg ctgttgctgt tgacccggaa ggtgctctgg acatcacccc ggacggtctg     360
gacgttaaag ttgacggtgt taccgttatg gttaacgacg actgggaact ggctgttaaa     420
gttgacccgt ctggtggtct ggactctacc gctggtggtc tgggtgtttc tgttgacgac     480
accctgctgg ttgaccaggg tgaactgggt gttcacctga ccagcaggg tccgatcacc      540 gctgactctt ctggtatcga cctggaaatc aacccgaaca tgttcaccgt taacacctct     600
accggttctg gtgttctgga actgaacctg aaagctcagg gtggtatcca ggctggttct     660
tctggtgttg gtgtttctgt tgacgaatct ctggaaatcg ttaacaacac cctggaagtt     720
aaaccggacc cgtctggccc actgaccgta agcgctaacg gtctgggtct gaaatacgac     780
tctaacaccc tggctgttac cgctggtgct ctgaccgttg ttggtggtgg ttctgttct      840 accccgatcg ctaccttcgt ttctggttct ccgtctctga acacctacaa cgctaccatc     900
gttaactctt cttctcaccc gttctcttgc gcttactacc tgcagcagtg gaacgttcag     960
ggtctgctgt tcacctctct gtacgttaaa ctggactcta ccaccatggg tacccgtccg    1020
ggtgacaact cttctgctaa cgctaaatgg ttcaccttct gggtttctgc ttacctgcag    1080
cagtgcaacc cgagcggtat ccaggcgggt accgtaagcc cgtctaccgc tgctctggct    1140
gacttcgaac cgatggctaa ccgttctgtt tcttctccgt ggacctactc tgctaacgct    1200
tactaccagc cgtcttcggg tgagttccag gtcttcaccc cggtcgttac cggtgcttgg    1260
aacccgggta acatcggtat ccgtgttctg ccggttccgg ttaccgcttc tggtgaccgt    1320
tacaccctgc tgtgctactc tctgcagtgc accaactctt ctatcttcaa cccggctaac    1380
tctggtacca tgatcgttgg tccggttctg tactcttgcc cggctgcttc tgttccgtaa    1440

<210> SEQ ID NO 2
<211> LENGTH: 1452
<212> TYPE: DNA
<213> ORGANISM: Fowl adenovirus

<400> SEQUENCE: 2
```

```
atgagcctcg gaagactccg agcccctaaa agaagacatt ccgaaaacgg gcagcccgag    60
tccgaagcgg gaccttcccc ggctccaatc aagcgcgcga acgcatggt gagagcatcc    120
cagcttgacc tggtttatcc tttcgattac gtggccgacc ccgtcggagg gctcaacccg    180
ccttttttgg gcggctccgg acccctagtg gaccagggcg gtcagcttac gctcaacgtc    240
accgatccca tcatcatcaa gaacagatcg gtggacttgg cccacgatcc cagtctcgat    300
gtcaacgccc aaggtcaact ggcggtggcc gttgaccccg aaggggccct ggacatcacc    360
cccgatggac tggacgtcaa ggtcgacgga gtaaccgtga tggtcaacga tgactgggaa    420
ctggccgtaa agtcgaccc gtccggcgga ttggattcca ctgcgggcgg actgggggtc    480
agcgtggacg acaccttgct cgtggatcag ggagaactgg gcgtacacct caaccaacaa    540
ggacccatca ctgccgatag cagtggtatc gacctcgaga tcaatcctaa catgttcacg    600
gtcaacacct cgaccggaag cggagtgctg gaactcaacc taaaagcgca gggaggcatc    660
caagccggca gttcgggagt gggcgttttc gtggatgaaa gcctagagat tgtcaacaac    720
acgctggaag tgaaaccgga tcccagcgga ccgcttacgg tctccgccaa tggcctaggg    780
ctgaagtacg acagcaatac cctggcggtg accgcgggcg cttttgaccgt agtaggaggg    840
ggaagcgtct ccacacccat cgctactttt gtctcgggaa gtcccagcct caacacctac    900
aatgccacga tcgtcaattc cagctcgcac cccttctctt gtgcctacta ccttcaacag    960
tggaacgtac aagggctcct ttttacctcc ctctacgtga aactggacag caccaccatg    1020
gggactcgcc ctggggacaa cagctccgcc aatgccaaat ggttccacctt ttgggtgtcc    1080
gcctatctcc agcaatgcaa cccctccggg attcaagcgg gaacggtcag cccctccacc    1140
gccgccctcg cggactttga acccatggcc aataggagcg tgtccagccc atggacgtac    1200
tcggccaatg catactatca accatccagc ggagaattcc aagtgttcac cccggtggta    1260
acgggtgcct ggaacccggg aaacataggg atccgcgtcc tcccagtgcc ggttacggcc    1320
tctggagacc gctacaccct tctatgctac agtttgcagt gcacgaactc gagcattttt    1380
aatccagcca acagcggaac tatgatcgtg ggacccgtgc tctacagctg ccagcagcc    1440
tccgtcccgt aa                                                        1452
```

<210> SEQ ID NO 3
<211> LENGTH: 17
<212> TYPE: DNA
<213> ORGANISM: Artificial Sequence
<220> FEATURE:
<223> OTHER INFORMATION: Forward primer for amplification of gene of
      fowl adenovirus Fiber-2 protein

<400> SEQUENCE: 3
ctccgggccc ctaaaag                                                   17

<210> SEQ ID NO 4
<211> LENGTH: 14
<212> TYPE: DNA
<213> ORGANISM: Artificial Sequence
<220> FEATURE:
<223> OTHER INFORMATION: Reverse primer for amplification of gene of
      fowl adenovirus Fiber-2 protein

<400> SEQUENCE: 4
gggacggagg ccgc                                                      14

<210> SEQ ID NO 5
<211> LENGTH: 32

```
<212> TYPE: DNA
<213> ORGANISM: Artificial sequence
<220> FEATURE:
<223> OTHER INFORMATION: Forward primer for amplification of gene of
      infectious bursal disease virus VP2 protein

<400> SEQUENCE: 5
ccggaattca tgacaaacct gcaagatcaa ac                                    32

<210> SEQ ID NO 6
<211> LENGTH: 33
<212> TYPE: DNA
<213> ORGANISM: Artificial sequence
<220> FEATURE:
<223> OTHER INFORMATION: Reverse primer for amplification of gene of
      infectious bursal disease virus VP2 protein

<400> SEQUENCE: 6
acgcgtcgac ttaccttagg gcccggatta tgt                                   33

<210> SEQ ID NO 7
<211> LENGTH: 38
<212> TYPE: DNA
<213> ORGANISM: Artificial sequence
<220> FEATURE:
<223> OTHER INFORMATION: Forward primer for amplification of gene of
      fowl adenovirus Fiber-2 protein

<400> SEQUENCE: 7
cgccatatga gcctcggaag actccgagcc cctaaaag                              38

<210> SEQ ID NO 8
<211> LENGTH: 31
<212> TYPE: DNA
<213> ORGANISM: Artificial sequence
<220> FEATURE:
<223> OTHER INFORMATION: Reverse primer for amplification of gene of
      fowl adenovirus Fiber-2 protein

<400> SEQUENCE: 8
cccaagcttt tacgggacgg aggctgctgg a                                     31
```

VACCINE COMPOSITION AND PREPARATION METHOD AND USE THEREOF

CROSS-REFERENCE OF RELATED APPLICATION

This application is a continuation of PCT Application Serial No. PCT/CN2017/109357, entitled "Vaccine Composition and Preparation Method and Use Thereof," filed on Nov. 3, 2017, which claims priority from a Chinese Application No. 201611091770.7, filed on Dec. 1, 2016, the contents of which are hereby incorporated herein in their entirety by this reference.

SEQUENCE LISTING

The instant application contains a Sequence Listing which has been filed electronically in ASCII format and is hereby incorporated by reference in its entirety. Said ASCII copy, created on Jan. 30, 2018, is named 17EAP0020CP-US_P8856US00_Sequence_Listing.txt and is 5.74 kilobytes in size.

FIELD OF TECHNOLOGY

The disclosure relates to a vaccine composition against fowl adenovirus and a preparation method and use thereof, belonging to the biomedical field.

BACKGROUND ART

A disease of fowl adenovirus (FADV) infection is an infectious disease caused by group I poultry adenovirus. FADV belongs to the Family Adenoviridae, of which genome is composed of nonsegmented linear double-stranded DNA.

FADV has a spherical structure without envelope, of which the virus particles in the infected cell nucleus are often in a lattice-like arrangement, each virus particle contains a single linear double-strand DNA of 36 kb, two line-like strands of DNA and core protein form a core with a diameter of 60-65 nm, encapsulated within the capsid. The capsid is icosahedrally symmetrical and consists of 252 capsid particles with a diameter of 8-10 nm. The capsid particles are arranged on face of a triangle with 6 on each side, wherein 240 are hexon (non-apex capsid particles) and the other twelve were penton bases (apex capsid particles, Penton protein). Each penton base is combined with two fiber projections (Fiber-1 and Fiber-2 proteins) with a length of 9-77.5 nm.

In recent years, the morbidity of diseases caused by FADV has been suddenly increased, especially for broiler chickens which are 3-5 weeks old, and in severe cases the mortality rate could suddenly rise to above 80%.

Vaccination is effective in preventing the disease. However, in the prior art, it is difficult to obtain high-titer virus due to the difficulty of culturing the fowl adenovirus, in particular, the large differences between different isolated strains, resulting in the fact that it is usually difficult to provide an ideal immunization effect with the prepared vaccine and bio-safety risks can also caused by incomplete inactivation in whole virus vaccines. The antigenic components of subunit vaccines in the prior art are hexon (240/252), which constitute the major component of the viral capsid. However, the immunological efficacy has been always low and no product has been developed.

Therefore, clinically, there is an urgent need to develop a vaccine composition with a good immunological effect that can effectively prevent the epidemic of the disease.

DESCRIPTION

In order to solve the deficiency of the prior art, the disclosure provides a fowl adenovirus immunogenic protein, a vaccine prepared therefrom and a preparation method and use of the vaccine, which can effectively prevent and/or treat infection of the fowl adenovirus.

The disclosure relates to a vaccine composition against fowl adenovirus, wherein the vaccine composition comprises an immune amount of fowl adenovirus antigen and a pharmaceutically acceptable carrier; wherein the fowl adenovirus antigen comprises a subunit antigen of the fowl adenovirus immunogenic protein as described in the present disclosure or a live vector recombined with gene of the fowl adenovirus immunogenic protein.

The present disclosure further relates to a vaccine composition, wherein the vaccine composition comprises an immune amount of fowl adenovirus Fiber-2 protein or an immune amount of a live vector recombined with gene of the fowl adenovirus Fiber-2 protein, and a pharmaceutically acceptable carrier.

The disclosure also relates to a preparation method of the vaccine composition, the preparation method comprises the following steps of: (1) cloning a gene of the fowl adenovirus protein of the present disclosure; (2) transforming and recombining the gene of the fowl adenovirus protein cloned in the step (1); (3) expressing the recombinant fowl adenovirus protein; (4) isolating and purifying the recombinant fowl adenovirus protein, and treating the purified recombinant fowl adenovirus protein with a non-ionic surfactant; and (5) mixing the fowl adenovirus protein with an adjuvant based on a certain ratio and emulsifying the resulting mixture.

The disclosure also relates to a use of the vaccine composition according to the disclosure in preparing medicine for treatment and prevention of diseases related to infection of fowl adenovirus.

The present disclosure is the first to prepare the vaccine composition by adopting the FADV Fiber-2 protein after bulk expression of the gene of selected FADV protein. The vaccine composition prepared by the FADV Fiber-2 protein can prevent and/or treat an outbreak of the fowl adenovirus, and the body of the animal after being immunized with the vaccine composition containing the protein can rapidly produce antibody. The vaccine composition has good prevention and control effect on infection of FADV alone or in combination with other viruses, with good biosecurity. The present disclosure is the first to prepare the vaccine composition by adopting the FADV Fiber-2 protein, which vaccine composition has good immunogenicity and can provide complete protection to the chickens, and can be used for preventing and/or treating the infection of various genotypes of fowl adenovirus in clinical practice.

DETAILED DESCRIPTION

Hereinafter, embodiments of the present disclosure will be described.

The term "fowl adenovirus" (FADV) belongs to the Family Adenoviridae, of which genome is composed of nonsegmented linear double-stranded DNA, of which clinical symptoms of sick chickens include collapsing, crouching, fluffy feathers, pale skin of cockscomb and face, and poor growth. The pathological changes are characterized by the syndrome of Catarrhal tracheitis and pericardial effusion.

The present disclosure further relates to a vaccine composition, wherein the vaccine composition includes an immune amount of fowl adenovirus Fiber-2 protein or an immune amount of a live vector recombined with gene of the fowl adenovirus Fiber-2 protein, and a pharmaceutically acceptable carrier.

The gene of fowl adenovirus Fiber-2 protein according to the present disclosure is also applicable to developments of expression vectors, live vectors, nucleic acid vaccines, diagnostic reagents, and other drugs for preventing and/or treating fowl adenoviruses.

The present disclosure relates to a recombinant vector that is capable of expressing a Fiber-2 protein encoded by a nucleotide sequence according to the present disclosure.

For the first time, the present disclosure has found that Fiber-2 protein, which is present in a very little amount on the surface of capsid particles of fowl adenovirus, has good immunogenicity, either the subunit antigen prepared therefrom or the live vector recombined with its gene can produce good immunological efficacy after immunization and provide a protection rate of 100% to chickens.

The "live vectors" refers to non-pathogenic microorganisms which carry and express a gene of an antigenic or antigenic determinant by mean of genetic engineering as to produce immunogenicity. The non-pathogenic microorganisms can be bacteria and viruses, viruses that are often used as viral live vectors include vaccinia virus, fowlpox virus, turkey herpes virus, adenovirus, pseudorabies virus, retrovirus, lentivirus; bacterial live vectors can include attenuated *Salmonella*, BCG, attenuated *Listeria monocytogenes*, attenuated *vibrio cholerae*, attenuated *Shigella, Lactococcus lactis, Lactobacillus plantarum*, and *Streptococcus gordonii*.

Live vectors recombined with gene of fowl adenovirus Fiber-2 protein according to the present disclosure can be in a form of a common live vector in this field, such as attenuated vaccine strains of recombinant Newcastle disease virus, recombinant poxvirus and recombinant *Salmonella*.

Because the live vector vaccine composition of the present disclosure combines the advantages of an inactivated vaccine and a live vaccine, it can ensure that the laying fowls can be protected in terms of the immunological efficacy, and immunological efficacy of the live vector vaccine composition is so strong that adjuvants may not be added.

The present disclosure relates to a transformant including an introduced recombinant vector according to the present disclosure.

The disclosure further relates to a vaccine composition of fowl adenovirus, wherein the vaccine composition includes an immune amount of fowl adenovirus antigen of the present disclosure and a pharmaceutically acceptable carrier; wherein the fowl adenovirus antigen includes a subunit antigen.

The term "vaccine composition" as used in the present disclosure refers to a pharmaceutical composition containing the immunogenicity of fowl adenovirus that can induce, stimulate or enhance an immune response of a chicken only against fowl adenoviruses.

The term "immune amount" should be understood as an "immunologically effective amount," also refers to an immunoprotective amount or an effective amount to produce an immune response, which is an amount of antigen effective to induce an immune response in a recipient, which immune amount is sufficient to prevent or ameliorate signs or symptoms of a disease including adverse health effects or complications of the disease. The immune response may be sufficient for diagnostic purposes or other tests or may be suitable for use in preventing signs or symptoms of a disease, including adverse health consequences caused by an infection caused by a pathogen, or complications of the disease. Humoral immunity or cell-mediated immunity or both may be induced. The immune response of the animal to the immunogenic composition may be assessed indirectly, for example, by measuring antibody titers and analyzing lymphocyte proliferation, or directly by monitoring signs or symptoms after challenge with wild-type strains, while protective immunity provided by the vaccine may be assessed by measuring, for example, clinical signs of subjects such as mortality, reduction in morbidity, temperature values, and overall physiological condition and overall health and performance of the subjects. The immune response may include, but are not limited to induction of cellular and/or humoral immunity.

The term "fowl adenovirus antigen" refers to any composition that contains at least one form of fowl adenovirus antigen which can induce, stimulate or enhance an immune responses against fowl adenovirus infection, the forms of the antigen include but are not limited to inactivated, attenuated or subunit antigens.

As an embodiment of the present disclosure, the fowl adenovirus Fiber-2 protein is a protein encoded by SEQ ID NO. 1.

As an embodiment of the present disclosure, the fowl adenovirus Fiber-2 protein is a protein encoded by SEQ ID NO. 2.

As an embodiment of the present disclosure, the AGP titer of the fowl adenovirus Fiber-2 protein is equal to or greater than 1:2.

As an embodiment of the present disclosure, the AGP titer of the fowl adenovirus Fiber-2 protein is between 1:2 and 1:16.

The term "pharmaceutically acceptable carrier" refers to all components other than the fowl adenovirus antigen in the vaccine composition of the present disclosure which are carriers or diluents that do not cause significant irritation to an organism and do not abrogate the biological activity and properties of the administered compounds, preferably an adjuvant. The term "adjuvant" may includes a compound selected from a group consisting of alhydrogel adjuvant, saponins e.g., Quil A. QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion, the polymers of acrylic or methacylic acid and the copolymers of maleic anhydride and alkenyl derivative. The term "emulsion" may be based in particular on light liquid paraffin oil (European Pharmacopoeia type); isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifier to form the emulsion. The emulsifiers are preferably nonionic surfactants, in particular esters of sorbitan, of mannide (e.g. anhydromannitol oleate), of glycol, of polyglycerol. of propylene glycol and of oleic, isostearic, ricinoleic or hydroxy-stearic acid, which are optionally ethoxylated, and polyoxypropylene-polyoxyethylene block copolymers, in particular the Pluronic products, especially L121. See Hunter et al., The Theory and Practical Application of Adjuvants (Ed. Stewart-Tull, D. E. S). John Wiley and Sons, NY, pp 51-94 (1995) and Todd et al. Vaccine 15:564-570 (1997). For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of the same book. The term "polymers of acrylic or methacrylic acid" preferably are the polymers of acrylic or methacrylic acid which are cross-linked, especially with polyalkenyl ethers of sugars or polyalcohols. These compounds are known by the term carbomer (Trade name, Carbopol) (Phameuropa Vol. 8, No. 2, June 1996). Persons skilled in the art can also refer to U.S. Pat. No. 2,909,462 which describes such acrylic polymers cross-linked with a polyhydroxylated compounds having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio. USA) are particularly appropriate. They are cross-linked with an allyl sucrose or with allyl pentaerythritol. Among them, there may be mentioned Carbopol 974P, 934P and 971 P, most preferably Carbopol 971P. For the term "copolymerrs of maleic anhydride and alkenyl derivative", EMA (Monsanto), which is the copolymer of maleic anhydride and ethylene, can also be considered. The dissolution of these polymers in water leads to an acid solution that will be neutralized, preferably to physiological pH, in order to give the adjuvant solution, into which the immunogenic, immunological or vaccine composition itself will be incorporated. The term "adjuvant" includes, but is not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314, muramyl dipeptide, and Gel adjuvant among many others. Preferably, the adjuvant includes one or more of alhydrogel adjuvant, saponins, water-in-oil emulsion, oil-in-water emulsion, water-in-oil-in-water emulsion, the polymers of acrylic or methacylic acid, the copolymers of maleic anhydride and alkenyl derivative, the RIBI adjuvant system, Block co-polymer, SAF-M, monophosphoryl lipid A, Avridine lipid-amine adjuvant, heat-labile enterotoxin from E. coli, cholera toxin, IMS 1314, muramyl dipeptide and Gel adjuvant.

As an embodiment of the present disclosure, the pharmaceutically acceptable carrier includes an adjuvant which includes one or more of (1) alhydrogel adjuvant, saponins, Avridine, DDA; (2) water-in-oil emulsion, oil-in-water emulsion, water-in-oil-in-water emulsion; or (3) the polymers of acrylic or methacylic acid, the copolymers of maleic anhydride and alkenyl derivative; and the RIBI adjuvant system, Block co-polymer, SAF-M, monophosphoryl lipid A, lipid-amine adjuvant, heat-labile enterotoxin from E. coli, cholera toxin, IMS 1314, muramyl dipeptide and Gel adjuvant.

Preferably, the saponin is Quil A, QS-21 or GPI-0100;

Preferably, the emulsions are SPT emulsion and MF59 emulsion, or the emulsions are formed by combination of oil and emulsifiers, the emulsions can be based in particular on light liquid paraffin oil; isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di-(caprylate/ caprate), glyceryl tri-(caprylate/caprate) or propylene glycol dioleate; esters of branched fatty acids or alcohols, in particular isostearic acid esters; the emulsifiers are nonionic surfactants, in particular esters of Polyoxyethylene fatty acid (e.g. oleic acid), of sorbitan, of mannide (e.g. anhydromannitol oleate), of glycol, of polyglycerol, of propylene glycol and of oleic, isostearic, ricinoleic or hydroxy-stearic acid, which are optionally ethoxylated, ethers of fatty alcohols and polyhydric alcohols (e.g. oleyl alcohol) and polyoxypropylene-polyoxyethylene block copolymers, in particular the Pluronic products, especially L121.

Preferably, the polymers of acrylic or methacrylic acid are compounds known by carbomer in which the polymers of acrylic or methacrylic acid which are cross-linked, especially with polyalkenyl ethers of sugars or polyalcohols, preferably, Carbopol 974P, 934P or 971 P.

Preferably, the copolymerrs of maleic anhydride and alkenyl derivative are copolymers EMA of maleic anhydride and ethylene.

Preferably, the adjuvant is a white oil adjuvant for preparation of water-in-oil emulsion.

The concentration of the adjuvant ranges from 5% to 70% V/V, preferably from 30% to 70% V/V, more preferably 66% V/V.

The disclosure further relates to a vaccine composition, wherein the vaccine composition includes an immune amount of Fiber-2 protein of the present disclosure or a functional variant thereof, and a pharmaceutically acceptable carrier.

As an embodiment of the present disclosure, the vaccine composition of the present disclosure includes an immune amount of the Fiber-2 protein according to the present disclosure, which is substantially encoded by a nucleotide sequence shown by SEQ ID NO.1, and a pharmaceutically acceptable carrier.

As an embodiment of the present disclosure, the vaccine composition of the present disclosure includes an immune amount of the Fiber-2 protein according to the present disclosure, which is substantially encoded by a nucleotide sequence shown by SEQ ID NO.2, and a pharmaceutically acceptable carrier.

The Fiber-2 protein of the disclosure may be prepared by any method known in the art, for example by recombinant expression of the Fiber-2 protein gene, the expression system used may be any known expression system, for example: eukaryotic expression systems, and prokaryotic expression systems. Alternatively, the Fiber-2 protein sequence may be synthesized directly.

As an embodiment of the present disclosure, the vaccine composition of the present disclosure includes a Fiber-2 protein antigen with an AGP titer that is equal to or greater than 1:2 or a functional variant thereof.

As an embodiment of the present disclosure, the vaccine composition of the present disclosure includes a Fiber-2 protein antigen with an AGP titer that is equal to or greater than 1:2, which is substantially encoded by a nucleotide sequence shown by SEQ ID NO.1.

As an embodiment of the present disclosure, the vaccine composition of the present disclosure includes a Fiber-2 protein antigen with an AGP titer that is equal to or greater than 1:2, which is substantially encoded by a nucleotide sequence shown by SEQ ID NO.2.

As an embodiment of the present disclosure, the vaccine composition of the present disclosure includes a Fiber-2 protein antigen with an AGP titer that is between 1:2 and 1:16 or a functional variant thereof.

As an embodiment of the present disclosure, the vaccine composition of the present disclosure includes a Fiber-2 protein antigen with an AGP titer that is between 1:2 and 1:16, which is substantially encoded by a nucleotide sequence shown by SEQ ID NO.1.

As an embodiment of the present disclosure, the vaccine composition of the present disclosure includes a Fiber-2 protein antigen with an AGP titer that is between 1:2 and 1:16, which is substantially encoded by a nucleotide sequence shown by SEQ ID NO.2.

As an embodiment of the present disclosure, the vaccine composition of the present disclosure includes a Fiber-2 protein antigen with an AGP titer of 1:4 or a functional variant thereof.

As an embodiment of the present disclosure, the vaccine composition of the present disclosure includes a Fiber-2 protein antigen with an AGP titer of 1:4, which is substantially encoded by a nucleotide sequence shown by SEQ ID NO.1.

As an embodiment of the present disclosure, the vaccine composition of the present disclosure includes a Fiber-2 protein antigen with an AGP titer of 1:4, which is substantially encoded by a nucleotide sequence shown by SEQ ID NO.2.

As an embodiment of the present disclosure, the vaccine composition further includes one or more other antigens including antigen of Newcastle disease virus, antigen of avian influenza virus, antigen of avian infectious bronchitis virus, antigen of infectious bursal disease virus, antigen of egg drop syndrome virus, antigen of avian reovirus, *Escherichia coli*, antigen of *avibacterium paragallinarum*, antigen of *Mycoplasma Synoviae*, antigen of *Mycoplasma gallisepticum*, antigen of *Pasteurella multocida*, antigen of Marek's disease virus, antigen of avian encephalomyelitis virus and antigen of infectious laryngotracheitis virus.

As a preferred embodiment of the present disclosure, the vaccine composition further includes one or more other antigens including inactivated antigen of Newcastle disease virus inactivated antigen, inactivated antigen of avian influenza virus, inactivated antigen of avian infectious bronchitis virus, infectious bursal disease virus antigen VP2 protein and inactivated antigen of egg drop syndrome virus.

As a preferred embodiment of the present disclosure, the antigens of Newcastle disease virus are inactivated antigens of N7a strain, the antigen of avian influenza virus are inactivated antigens of SZ strain, the antigen of avian infectious bronchitis virus are inactivated antigen of M41 strain, the antigen of infectious bursal disease virus are VP2 protein and the antigen of egg drop syndrome virus are inactivated antigens of AV-127 strain.

As an embodiment of the present disclosure, the AGP titer of the Fiber-2 protein of the fowl adenovirus is between 1:2 and 1:16, the content of the antigens of the Newcastle disease virus is $10^{8.0}$-$10^{9.0}$ $EID_{50}$/0.1 ml before inactivation, the content of the avian influenza virus is $10^{6.5}$-$10^{8.5}$ $EID_{50}$/0.1 ml before inactivation, the content of the avian infectious bronchitis virus is $10^{6.0}$-$10^{7.0}$ $EID_{50}$/0.1 ml before inactivation, and the AGP titer of the VP2 protein of the avian infectious bursal disease virus antigen is between 1:16 and 1:128, and the content of the antigens of egg drop syndrome virus antigen is $10^{7.0}$-$10^{8.0}$ $EID_{50}$/0.1 ml before inactivation.

As a preferred embodiment of the present disclosure, the AGP titer of the Fiber-2 protein of the fowl adenovirus is between 1:2 and 1:16, the content of the antigens of the Newcastle disease virus is $10^{8.0}$$EID_{50}$/0.1 ml before inactivation, the content of the avian influenza virus is $10^{8.0}$$EID_{50}$/0.1 ml before inactivation, the content of the avian infectious bronchitis virus is $10^{6.0}$ $EID_{50}$/0.1 ml before inactivation, the AGP titer of and the VP2 protein of the avian infectious bursal disease virus antigen is 1:16, and the content of the antigens of egg drop syndrome virus antigen is $10^{7.0}$ $EID_{50}$/0.1 ml before inactivation.

As an embodiment of the present disclosure, the pharmaceutically acceptable carrier includes drugs, immunostimulants, antioxidants, surfactants, colorants, volatile oils, buffers, dispersants, propellants and preservatives; the immunostimulants include α-interferon, β-interferon, γ-interferon, granulocyte-macrophage colony stimulating factor (GM-CSF), macrophage colony stimulating factor (M-CSF) and interleukin 2 (IL2).

The vaccine composition of the present disclosure may be further used conjunctly with other pathogens or antigens to prepare combined vaccines or complex vacancies against various diseases including FADV infection.

The term "combined vaccine" refers to a vaccine prepared with the virus mixture by mixing the FADV in the present disclosure with at least one other different virus. The term "complex vaccine" refers to a vaccine prepared from FADV and bacterium. For example, the FADV in the present disclosure may be mixed or combined with Newcastle disease virus, avian infectious bronchitis virus, avian influenza virus, infectious bursal disease virus, egg drop syndrome virus, avian reovirus and/or *Escherichia coli, avibacterium paragallinarum, Mycoplasma Synoviae* and *Mycoplasma gallisepticum.*

The vaccine composition of the disclosure may further be added with other reagents.

As an embodiment of the present disclosure, the vaccine composition further includes drugs, immunostimulants, antioxidants, surfactants, colorants, volatile oils, buffers, dispersants, propellants, and preservatives.

Preferably, the immunostimulants include α-interferon, β-interferon, γ-interferon, granulocyte-macrophage colony stimulating factor (GM-CSF), macrophage colony stimulating factor (M-CSF) and interleukin 2 (IL2).

Methods well known in the art may be used to prepare such compositions.

The disclosure further relates to a preparation method of the vaccine composition, the preparation method includes the following steps of: (1) cloning a gene of the fowl adenovirus Fiber-2 protein of the present disclosure; (2) transforming and recombining the gene of the fowl adenovirus protein cloned in the step (1) in order to obtain *E Coli* recombined with Fiber-2 protein; (3) expressing the recombinant fowl adenovirus Fiber-2 protein; (4) isolating and purifying the recombinant fowl adenovirus Fiber-2 protein, and treating the purified recombinant fowl adenovirus Fiber-2 protein with a non-ionic surfactant; and (5) mixing the fowl adenovirus Fiber-2 protein with an adjuvant and emulsifying the resulting mixture.

The disclosure further relates to a use of the vaccine composition in preparing medicine for prevention and treatment of infection of fowl adenovirus.

The objects which the medicine for prevention and treatment of infection of fowl adenovirus is administered to include chickens.

The term "prevention and/or treatment" when referring to fowl adenovirus infection refers to inhibition of replication and spread of the fowl adenovirus or prevention of the fowl adenovirus from colonizing its host, and alleviation of disease or symptoms of illness of the fowl adenovirus. If the viral load is reduced, the severity of the illness is reduced, and/or the food intake and/or growth are increased, then it can be considered that the treatment has achieveed a therapeutic effect.

The description of the present disclosure is further provided as follows with reference to the specific embodiments, and features and advantages of the present disclosure will become more apparent from the following description. However, these embodiments are merely exemplary and do not limit the scope of the present disclosure in any way. It should be understood by a person skilled in the art that modifications or alternatives to details and forms of the technical solution of the present disclosure without deviation from the spirit and scope of the present disclosure will be allowed, while those modifications and alternatives should all fall within the scope of the present disclosure.

The chemical reagents used in the examples of the present disclosure are of analytical grade and are purchased from Sinopharm Group Co. Ltd.

In order to make the present disclosure more understandable, the present disclosure will be further described with reference to specific embodiments. The experimental methods described in the present disclosure are conventional methods unless otherwise specified. The biological materials are commercially available unless otherwise specified.

Example 1 Construction of Expression Vector of pET28a_FADV_Fiber-2

1, Extraction of FADV DNA

A plasmid extraction kit was purchased from TIANGEN BIOTECH; T4 DNA Ligase was purchased from BioLab; pET28a plasmid was purchased from Novagen; an agarose gel recovery kit was purchased from TIANZE BIOTECH, other reagents are analytically pure.

According to the manual of the virus DNA extraction kit, 0.2 ml of the Fowl Adenovirus FAV-HN strain was used. The FAV-HN strain (Fowl aviadenovirus, strain FAV-HN) has been deposited in the China Center for Type Culture Collection on Feb. 29, 2016, of which the accession number is CCTCC NO. V201609 and the address is Wuhan University, Wuhan, China. Chicken liver suspension was placed in a 1.5 ml sterile centrifuge tube, and added with 0.4 ml of VB buffer, mixed well by vortexing, and let stand at room temperature for 10 minutes. 0.45 ml of AD buffer was added in the above sample solution and mixed strongly. The VB column was placed in a 2 ml collection tube and 0.6 ml of the mixture was added to the VB column, which is then centrifuged at 14,000 g for 1 minute. The remaining mixture was added to the VB column which was then centrifuged at 14,000 g for 1 minute, the 2 ml collection tube was discarded and the VB column was placed into a new 2 ml collection tube. 0.4 ml of Wash buffer 1 was added into the VB column which was then centrifuged at 14000 g for 30 seconds, 0.6 ml Wash buffer was added in VB column, centrifuged at 14000 g for 30 seconds, and centrifuged without adding any Wash buffer for 3 minutes. 50 µl RNase free water was added to the center of membrane and let stand for 3 minute, centrifuged at 14000 g for 1 minute, the centrifuged liquid was DNA genome.

2. Amplification of Fiber-2 Protein Gene

Oligonucleotide primers were synthesized based on the conserved region sequences at the 5' and 3' ends of the Fiber-2 protein gene and subjected to PCR. Primer sequences are shown in Table 1.

TABLE 1

| amplification of Fiber-2 protein gene | |
|---|---|
| Fiber2-f (SEQ ID NO. 3) | CTCCGGGCCCCTAAAAG |
| Fiber2-r ( SEQ ID NO. 4) | CGGGACGGAGGCCGC |

The PCR product was sent to Invitrogen Corporation for sequencing, and codon optimization was performed to the Fiber-2 protein gene according to the sequencing result, the sequence of the optimized Fiber-2 protein gene is shown in SEQ ID NO. 1.

3. Construction of Expression Vector

The optimized Fiber-2 protein gene was sent to Genome Biosciences Co., Ltd. for full sequence synthesis and linked into pET28a plasmid respectively. The linked plasmid was transformed into *E. coli* BL21 (DE3). The single clone was picked up and cultured in LB medium containing 100 µg/ml of kanamycin overnight. The plasmid was extracted and sequenced. The positive clone was pET28a_FADV_Fiber-2 expression strain.

Example 2 Preparation of 2 Fiber-2 Protein

The pET28a_FADV Fiber-2/*E. coli* BL21 (DE3) strain prepared in Example 1 was inoculated into LB medium containing 50-100 µg/ml of kanamycin at an inoculum amount of 1% (V/V), and cultured with shaking at 37° C. When OD600=0.4-0.6, the sample was placed at 28° C. for 30 minutes. Isopropyl-β-D-1-thiogalactopyranoside (IPTG) was added to a final concentration of 0.1-1.0 mM and the sample was cultured with shaking at 28° C. for 24 hours. After cultivation, the bacteria were harvested and resuspended in physiological saline solution (8 g sodium chloride, 0.2 g potassium chloride, 1.44 g disodium hydrogen phosphate, 0.24 g potassium dihydrogen phosphate, adjusted to pH 7.4 with a final volume of 1 L), centrifuged after ultrasonic decomposition, and the supernatant was obtained. The expression product had a higher content of the soluble target protein, the AGP titer of Fiber-2 protein reached 1:64, and the endotoxin had a content of $0.48 \times 10^5$ EU/ml.

Example 3 Clearance of Endotoxin in Fiber-2 Protein Expressed in *E. coli*

0.5 ml of the solution to be treated and Triton X-114 (5 µl) at a final concentration of 1% (v/v) were added to a 1.5 ml centrifuge tube and vortexed. The sample was placed on ice for 5 minutes. After vortexing the cooled sample, the centrifuge tube was immediately put in a 37° C. water bath for 5 min to create new two phases. Then, the sample was centrifuged at 37° C. for 60 seconds. After centrifugation, the target protein will remain in the upper layer, while the endotoxin-containing detergent will remain in the shape of an oil droplet at the bottom of the centrifuge tube. The entire operation went through 3 cycles. It was measured that the AGP titer of Fiber-2 protein reached 1:64, and the endotoxin had a content of $0.008 \times 10^5$ EU/ml.

The results showed that Triton X-114 could eliminate the residual endotoxin in the recombinant protein and had no effect on the immunogenicity of Fiber-2.

Example 4 Preparation of Subunit Vaccine of Fowl Adenovirus Fiber-2 Protein

The fiber-2 protein purified according to the method of Example 3 was slowly added to the white oil adjuvant, while the motor was started, stirred at 17500 r/min for 5 min. 1% thimerosal solution was added before termination of stirring to a final concentration of 0.01%. The component ratios are shown in Table 2.

TABLE 2

Component ratios of the subunit vaccine of fowl
adenovirus Fiber-2 Protein

| Component | Vaccine 1 | Vaccine 2 | Vaccine 3 |
|---|---|---|---|
| Fiber-2 protein (AGP titer) | 1:2 | 1:4 | 1:16 |
| White oil adjuvant (v/v %) | 66% | 66% | 66% |

Example 5 Safety Test of the Subunit Vaccine of the Fowl Adenovirus Fiber-2 Protein 60 21-day-old SPF chickens were divided into 4 groups, that is to say, 15 chickens per group, the chickens in groups 1-3 were immunized by subcutaneous injection in necks with corresponding vaccine 1, vaccine 2, vaccine 3 prepared in Example 4, respectively, at an immune amount of 0.6 ml, and the chickens in group 4 were injected with 0.6 ml of physiological saline solution by subcutaneous injection, as a blank control. The chickens were fed under the same conditions, and observed starting from the third week after immunization for clinical symptoms, weight gain rate and mortality. Five chickens were dissected respectively at 3 weeks, 4 weeks and 5 weeks to observe whether the inoculation site formed gross lesions. The results showed (see Table 3, Table 4) that, no clinical symptoms and death could be observed in the vaccination group (vaccine 1-3), in addition, the weight gain rate of the vaccination group and the control group showed no significant difference, and no granulomas were formed, indicating that it is safe to immunize chickens with the subunit vaccine of the fowl adenovirus Fiber-2 protein of the present disclosure.

TABLE 3

Clinical symptoms and number of deaths for safety test of the
subunit vaccine of the fowl adenovirus Fiber-2 Protein

| Group | Number of chickens | Clinical symptoms and number of deaths after immunization | |
|---|---|---|---|
| | | Clinical Symptoms | death |
| 1 | 15 | 0/15 | 0/15 |
| 2 | 15 | 0/15 | 0/15 |
| 3 | 15 | 0/15 | 0/15 |
| 4 | 15 | 0/15 | 0/15 |

TABLE 4

Chicken weight change and formation of granulomas for safety
test of the subunit vaccine of the fowl adenovirus Fiber-2 Protein

| Group | Number of chickens | Weight (g, mean ± SD) | | Formation of granulomas after immunization | | |
|---|---|---|---|---|---|---|
| | | Before immunization | End up at the third week after immunization | 3 weeks | 4 weeks | 5 weeks |
| 1 | 15 | 324 ± 16.2 | 576 ± 15.2 | 0/5 | 0/5 | 0/5 |
| 2 | 15 | 326 ± 15.5 | 578 ± 17.5 | 0/5 | 0/5 | 0/5 |
| 3 | 15 | 327 ± 16.8 | 579 ± 16.6 | 0/5 | 0/5 | 0/5 |
| 4 | 15 | 328 ± 20.2 | 579 ± 21.2 | 0/5 | 0/5 | 0/5 |

Example 6 Immunogenicity Test of the Subunit Vaccine of the Fowl Adenovirus Fiber-2 Protein 40 21-day-old SPF chickens were divided into 4 groups, that is to say, 10 chickens per group, the chickens in groups 5-7 were immunized by subcutaneous injection in necks with corresponding vaccine 1, vaccine 2, vaccine 3 prepared in Example 4, respectively, at an immune amount of 0.3 ml, and the chickens in group 8 were injected with 0.3 ml of physiological saline solution by subcutaneous injection, as a blank control. All experimental chickens were fed in isolation. On the 21st day after immunization, the chickens were challenged by intramuscular injection of the virus solution of FAV-HN strain, and observed for 14 days. The numbers of incidence and death, and rate for protection were recorded. The results are shown in Table 5.

Example 5 Immunogenicity test of the subunit vaccine of the
fowl adenovirus Fiber-2 Protein

| | Immune dose | Results of challenge | | |
|---|---|---|---|---|
| Group | (ml per chicken) | Number of chickens | Number of incidence | Number of deaths | Protection rate |
| 5 | 0.3 | 10 | 0/10 | 0/10 | 100% |
| 6 | 0.3 | 10 | 0/10 | 0/10 | 100% |
| 7 | 0.3 | 10 | 0/10 | 0/10 | 100% |
| 8 | 0.3 | 10 | 10/10 | 10/10 | 0 |

The results showed that chickens in the 8th group, i.e. control group were all died, while the groups 5-7, immunization group had a good immune protection effect on the immunized chickens with excellent immunization effect. The results showed that the subunit vaccine of the fowl adenovirus Fiber-2 protein with an AGP tier that was not less than 1:2 could provide effective immune protection for chickens.

Example 7 Cross-Protection Test of the Subunit Vaccine of the Fowl Adenovirus Fiber-2 Protein 100 21-day-old SPF chickens were divided into 10 groups, that is to say, 10 chickens per group, the chickens in groups 9-13 were immunized respectively by subcutaneous injection in necks with corresponding vaccine 1 prepared in Example 4 at an immune amount of 0.3 ml, and the chickens in group 14-18 s were injected with 0.3 ml of physiological saline solution by subcutaneous injection, as a blank control. All experimental chickens were fed in isolation, and on the 21st day after immunization, the chickens were challenged by intramuscular injection of the heterotopic serotype of virus solution, and observed for 14 days. The numbers of incidence and death, and rate for protection were recorded. The results are shown in Table 6.

TABLE 6

Result of cross-protection test of the subunit vaccine of the fowl adenovirus Fiber-2 Protein

| Group | Immune dose (ml per chicken) | Number of chickens | Serotype of challenge | Number of incidence | Number of deaths | Protection rate |
|---|---|---|---|---|---|---|
| 9 | 0.3 | 10 | Type 2 | 0/10 | 0/10 | 100% |
| 10 | 0.3 | 10 | Type 3 | 0/10 | 0/10 | 100% |
| 11 | 0.3 | 10 | Type 5 | 0/10 | 0/10 | 100% |
| 12 | 0.3 | 10 | Type 8 | 0/10 | 0/10 | 100% |
| 13 | 0.3 | 10 | Type 11 | 0/10 | 0/10 | 100% |
| 14 | 0.3 | 10 | Type 2 | 4/10 | 2/10 | 60% |
| 15 | 0.3 | 10 | Type 3 | 5/10 | 4/10 | 50% |
| 16 | 0.3 | 10 | Type 5 | 4/10 | 4/10 | 60% |
| 17 | 0.3 | 10 | Type 8 | 3/10 | 2/10 | 70% |
| 18 | 0.3 | 10 | Type 11 | 8/10 | 7/10 | 20% |

The results showed that chickens in groups 14-18, i.e. control groups had different levels of incidence or death, and the groups 9-13, i.e. immunization groups had a good immune protection effect on the immunized chickens with excellent immunization effect. The results showed that the subunit vaccine of the fowl adenovirus Fiber-2 protein with an AGP tier that was not less than 1:2 could provide effective immune protection for chickens against different serotypes of adenovirus.

Example 8 Preparation of Antigens of Newcastle Disease Virus

Newcastle disease virus (genotype VII), N7a strain deposited in China Center for Type Culture Collection on Oct. 19, 2015 with an accession number CCTCC NO: V201545 and a deposition address that is Wuhan University, Wuhan, China, was diluted appropriately with sterile saline so as to inoculate susceptible chicken embryos which are 10-11 days old at 0.1 ml per embryo and placed at 37° C. after inoculation for subsequent incubation. Allantoic fluid was harvested from chicken embryos which were died within 48 to 120 hours after inoculation and survived at 120 hours after inoculation after inoculation, the virus content determined was $10^{8.0}$ $EID_{50}$/0.1 ml. Formaldehyde solution with a final concentration of 0.1% (v/v) was added into the sample which is then placed at 37° C. to be inactivated, and stirred once every 4-6 h during the process, and stored after 16 h of complete inactivation.

Example 9 Preparation of Antigens of Avian Influenza Virus

H9 subtype of avian influenza virus SZ strain (disclosed in Chinese patent application CN103789272A, the SZ strain is Aivan Influenza Virus H9 subtype Strain SZ, of which the accession number is China Center for Type Culture Collection (CCTCC) NO. V201240, said SZ strain was deposited in CCTCC under the Budapest Treaty on Sep. 16, 2012, of which the address is Wuhan University, Wuhan City, Hubei Province) as a virus species was picked and diluted with sterile saline to $10^{-3}$ (0.1 ml of virus solution was added to 0.9 ml sterile saline, and then diluted 2 more times after shaking and mixing). The diluted virus solution was inoculated into 10-day-old susceptible chicken embryos (hatched from SPF hatching eggs purchased from Beijing Meiliyaweitong Experimental Animal Technology Co., Ltd) via the allantoic cavity at 0.1 ml (containing $10^5 EID_{50}$) per embryo. The pinhole was sealed after inoculation, and the chicken embryos were placed at 36-37° C. for subsequent incubation without turning over eggs. After 96 hours, the eggs were removed and placed upright with upward gas chambers, at 2-8° C. and cooled for 12-24 hours. Allantoic fluid was harvested from the cooled chicken embryos. The virus content determined was $10^{8.5} EID_{50}$/0.1 ml. Formaldehyde solution with a final concentration of 0.1% (v/v) was added into the sample which is then placed at 37° C. to be inactivated, and stirred once every 4-6 h during the process, and stored after 24 h of complete inactivation.

Example 10 Preparation of Antigens of Avian Infectious Bronchitis Virus

Avian infectious bronchitis virus M41 strain (purchased from the China Veterinary Drug Administration) was diluted appropriately (to $10^{-2}$ or $10^{-3}$) with sterile saline so as to inoculate susceptible chicken embryos which are 10-11 days old at 0.1 ml per embryo and placed at 36-37° C. after inoculation for subsequent incubation. Allantoic fluid was harvested from chicken embryos which were died within 24 to 48 hours after inoculation and survived at 48 hours after inoculation, the virus content determined was $10^{6.0}$ $EID_{50}$/0.1 ml. Formaldehyde solution with a final concentration of 0.1% (v/v) was added into the sample which is then placed at 37° C. to be inactivated, and stirred once every 4-6 h during the process, and stored after 16 h of complete inactivation.

Example 11 Preparation of Antigens of Infectious Bursal Disease Virus (IBDV)

1. Preparation of VP2 cDNA

The IBDV RNA was extracted from the bursa of Fabricius of SPF chickens infected with very virulent IBDV Chengdu strain by virus RNA extraction kit and reverse transcribed with random primers. Oligonucleotide primers were synthesized based on the sequences of conserved region at the 5' and 3' ends of the VP2 protein gene, and amplified by PCR, and recovered by the agarose gel recovery kit and stored at −20° C. The sequences of the synthesized oligonucleotide primers are shown in Table 7.

TABLE 7

Primers for gene of IBDV VP2 protein

| | |
|---|---|
| VP2-EcoR1-f (SEQ ID NO. 5) | CCGGAATTCATGACAAACCTGCAAGATCAAC |
| VP2-Sall-r (SEQ ID NO. 6) | ACGCGTCGACTTACCTTAGGGCCCGGATTATGT |

2. Construction of pColdIII_VP2/*E. Coli* BL21 (DE3) Strain

The VP2 cDNA prepared above was double-digested, and the digested fragment was ligated into the pCold III vector. The ligated product was directly transformed into *E. coli* BL21 (DE3) and spread on a solid LB medium containing 100 μg of ampicillin and cultureed overnight, the colonies that grew were the pCold III_VP2/*E. coli* BL21 (DE3) strain.

3. Preparation of Infectious Bursal Disease Virus VP2 Protein

The strain would be cultured in a culture tank with natural ventilation, which was filled with 70% culture medium and peanut oil defoamer according to the volume. After sterilization, the seed solution of pColdIII_VP2/*E. coli* BL21 (DE3) strain was inoculated at 2%-4% of the amount of culture medium and cultured at 37° C. 0.2 mol/L α-lactose was added in when the OD600 value of the solution reached 0.6-1.0, so that the final concentration reached 0.02 mol/L, then continued to be cultured for 5-8 h.

After cultivation, the bacteria were collected by centrifugation, resuspended, ultrasonicated, and centrifuged to collect the supernatant. After precipitation with ammonium sulfate, VP2 protein solution was collected.

Example 12 Preparation of Antigens of Egg Drop Syndrome Virus

Egg drop syndrome virus AV-127 strain (purchased from the China Veterinary Drug Administration) was diluted with sterile saline in a certain ratio. The sample was inoculated into 10-day-old susceptible duck embryos via the allantoic cavity at 0.1 ml per embryo. After inoculation, the duck embryos were placed at 36-37° C. for subsequent incubation. The duck embryos that died within the first 24 hours were discarded. The rest of the eggs were lighted every 6-8 hours since then to pick up the dead duck embryos. All the duck embryos were picked up after 120 hours and placed upright with upward gas chambers, and cooled at 2-8° C. for 12-24 hours. The allantoic fluid then was harvested under a sterile condition, and the virus content determined was $10^{8.5}EID_{50}/0.1$ ml. Formaldehyde solution with a final concentration of 0.2% (v/v) was added into the sample which is then placed at 37° C. to be inactivated, and stirred once every 4-6 during the process, and stored after 16 h of complete inactivation.

Example 13 Preparation of Combined Vaccine of Fowl Adenovirus

The fiber-2 protein purified according to Example 3 was mixed with antigens of Newcastle disease virus prepared according to Example 8, avian influenza virus prepared according to Example 9, avian infectious bronchitis virus prepared according to Example 10, infectious bursal disease virus prepared according to Example 11, and egg drop syndrome virus prepared according to Example 12 in a certain ratio, respectively, and added to the white oil adjuvant, while the motor was started, stirred at 17500 r/min for 5 min. 1% thimerosal solution was added before termination of stirring to a final concentration of 0.01%. The component ratios are shown in Table 8, 9, 10, 11.

TABLE 8

Component ratios of fowl adenovirus two-combined vaccine

| Component | Vaccine 4 | Vaccine 5 | Vaccine 6 | Vaccine 7 | Vaccine 8 |
|---|---|---|---|---|---|
| Fiber-2 protein (AGP tier) | 1:2 | 1:4 | 1:8 | 1:16 | 1:2 |
| Antigen of N7a strain ($EID_{50}/0.1$ ml) | $10^{8.0}$ | — | — | — | — |
| Antigen of SZ strain ($EID_{50}/0.1$ ml) | — | $10^{8.0}$ | — | — | — |
| Antigen of M41 strain ($EID_{50}/0.1$ ml) | — | — | $10^{6.0}$ | — | — |
| VP2 protein (AGP titer) | — | — | — | 1:16 | — |
| Antigen of AV-127 strain ($EID_{50}/0.1$ ml) | — | — | — | — | $10^{7.0}$ |
| White oil adjuvant (v/v %) | 66% | 66% | 66% | 66% | 66% |

TABLE 9

Component ratios of fowl adenovirus three-combined vaccine

| Component | Vaccine 9 | Vaccine 10 | Vaccine 11 | Vaccine 12 |
|---|---|---|---|---|
| Fiber-2 protein (AGP tier) | 1:4 | 1:8 | 1:16 | 1:2 |
| Antigen of N7a strain ($EID_{50}$/0.1 ml) | $10^{8.0}$ | $10^{8.0}$ | $10^{8.0}$ | $10^{8.0}$ |
| Antigen of SZ strain ($EID_{50}$/0.1 ml) | $10^{8.0}$ | — | — | — |
| Antigen of M41 strain ($EID_{50}$/0.1 ml) | — | $10^{6.0}$ | — | — |
| VP2 protein (AGP titer) | — | — | 1:16 | — |
| Antigen of AV-127 strain ($EID_{50}$/0.1 ml) | — | — | — | $10^{7.0}$ |
| White oil adjuvant (v/v %) | 66% | 66% | 66% | 66% |

TABLE 10

Component ratios of fowl adenovirus four-combined vaccine

| Component | Vaccine 13 | Vaccine 14 | Vaccine 15 | Vaccine 16 | Vaccine 17 |
|---|---|---|---|---|---|
| Fiber-2 protein (AGP tier) | 1:4 | 1:8 | 1:16 | 1:2 | 1:4 |
| Antigen of N7a strain ($EID_{50}$/0.1 ml) | $10^{8.0}$ | $10^{8.0}$ | $10^{8.0}$ | $10^{8.0}$ | $10^{8.0}$ |
| Antigen of SZ strain ($EID_{50}$/0.1 ml) | $10^{8.0}$ | — | — | $10^{8.0}$ | $10^{8.0}$ |
| Antigen of M41 strain ($EID_{50}$/0.1 ml) | $10^{6.0}$ | $10^{6.0}$ | $10^{6.0}$ | — | — |
| VP2 protein (AGP titer) | — | 1:16 | — | 1:16 | — |
| Antigen of AV-127 strain ($EID_{50}$/0.1 ml) | — | — | $10^{7.0}$ | — | $10^{7.0}$ |
| White oil adjuvant (v/v %) | 66% | 66% | 66% | 66% | 66% |

TABLE 11

Component ratios of fowl adenovirus four-combined vaccine

| Component | Vaccine 18 | Vaccine 19 |
|---|---|---|
| Fiber-2 protein (AGP tier) | 1:8 | 1:16 |
| Antigen of N7a strain ($EID_{50}$/0.1 ml) | $10^{8.0}$ | $10^{8.0}$ |
| Antigen of SZ strain ($EID_{50}$/0.1 ml) | $10^{8.0}$ | $10^{8.0}$ |
| Antigen of M41 strain ($EID_{50}$/0.1 ml) | $10^{6.0}$ | $10^{6.0}$ |
| VP2 protein (AGP titer) | 1:16 | — |
| Antigen of AV-127 strain ($EID_{50}$/0.1 ml) | — | $10^{7.0}$ |
| White oil adjuvant (v/v %) | 66% | 66% |

Example 14 Immunogenicity Test of the Combined Vaccine of the Fowl Adenovirus

1. Immunogenic Test of Fowl Adenovirus Part 170 21-day-old SPF chickens were divided into 17 groups, that is to say, 10 chickens per group, the chickens in groups 19-34 were immunized by subcutaneous injection in necks with corresponding vaccines 4-19 prepared in Example 13 at an immune amount of 0.3 ml per chicken, respectively, and the chickens in group 35 were injected with 0.3 ml of physiological saline solution by subcutaneous injection, as a blank control. All experimental chickens were fed in isolation. On the 21st day after immunization, the chickens were challenged by intramuscular injection of the virus solution of FAV-HN strain, and observed for 14 days. The numbers of incidence, death and rate for protection were recorded. The results are shown in Table 12.

TABLE 12

Result of immunogenicity test of the fowl adenovirus part of the combined vaccine of the fowl adenovirus

| Group | Immune dose (ml per chicken) | Number of chickens | Results of challenge | | Protection rate |
|---|---|---|---|---|---|
| | | | Number of incidence | Number of deaths | |
| 19 | 0.3 | 10 | 0/10 | 0/10 | 100% |
| 20 | 0.3 | 10 | 0/10 | 0/10 | 100% |
| 21 | 0.3 | 10 | 0/10 | 0/10 | 100% |
| 22 | 0.3 | 10 | 0/10 | 0/10 | 100% |
| 23 | 0.3 | 10 | 0/10 | 0/10 | 100% |
| 24 | 0.3 | 10 | 0/10 | 0/10 | 100% |
| 25 | 0.3 | 10 | 0/10 | 0/10 | 100% |
| 26 | 0.3 | 10 | 0/10 | 0/10 | 100% |
| 27 | 0.3 | 10 | 0/10 | 0/10 | 100% |
| 28 | 0.3 | 10 | 0/10 | 0/10 | 100% |
| 29 | 0.3 | 10 | 0/10 | 0/10 | 100% |
| 30 | 0.3 | 10 | 0/10 | 0/10 | 100% |
| 31 | 0.3 | 10 | 0/10 | 0/10 | 100% |
| 32 | 0.3 | 10 | 0/10 | 0/10 | 100% |
| 33 | 0.3 | 10 | 0/10 | 0/10 | 100% |
| 34 | 0.3 | 10 | 0/10 | 0/10 | 100% |
| 35 | 0.3 | 10 | 10/10 | 10/10 | 0 |

The results showed that all of vaccine 4-19 in immunization groups could produce good immune protection on Day 21 after immunization. The results showed that the oil emulsion combined vaccine in which the fowl adenovirus Fiber-2 protein was prepared as the antigen, could provide complete protection to chickens 2. Immunogenic Test of Newcastle Disease Virus Part 130 21-day-old SPF chickens were divided into 13 groups, that is to say, 10 chickens per group, the chickens in groups 36-34 were immunized by subcutaneous injection in necks with corresponding vaccine 4 and vaccines 10-19 prepared in Example 13 at an immune amount of 20 μl per chicken, respectively, and the chickens in group 48 were injected with 20 μl of physiological saline solution by subcutaneous injection, as a blank control. All the experimental chickens were fed in isolation. On the 21st day after immunization, the blood samples of the immunized chickens in groups 36-47 together with that of the control chickens in the 48th group were collected and corresponding serum samples were separated. HI antibody of the Newcastle disease virus was detected. Meanwhile the chickens were challenged by intramuscular injection of the virus solution of virulent Newcastle disease virus HN1101 strain, and observed for 14 days. The numbers of incidence, death and rate for protection were recorded. The results are shown in Table 13.

0.3 ml of physiological saline solution by subcutaneous injection, as a blank control. All the experimental chickens were fed in isolation. On the 21st day after immunization, the blood samples of the immunized chickens in groups 49-56 together with that of the control chickens in the 57th group were collected, and corresponding serum samples were separated. HI antibody of the H9 subtype of avian influenza virus was detected. Meanwhile the chickens were challenged by intramuscular injection of the virus solution of SZ strain at 0.2 ml (containing $10^{7.0}$ $EID_{50}$) per chicken.

TABLE 13

Result of immunogenicity test of the Newcastle disease virus part of the combined vaccine of the fowl adenovirus

| | | | HI antibody detection | | Results of challenge | | |
| --- | --- | --- | --- | --- | --- | --- | --- |
| | Immune | Number | result (log$_2$) | | Number | | |
| Group | dose (μl per chicken) | of chickens | Before immunization | Day 21 after immunization | of incidence | Number of deaths | Protection rate |
| 36 | 20 | 10 | 0 | 8.0 | 0/10 | 0/10 | 100% |
| 37 | 20 | 10 | 0 | 8.1 | 0/10 | 0/10 | 100% |
| 38 | 20 | 10 | 0 | 8.1 | 0/10 | 0/10 | 100% |
| 39 | 20 | 10 | 0 | 8.0 | 0/10 | 0/10 | 100% |
| 40 | 20 | 10 | 0 | 8.1 | 0/10 | 0/10 | 100% |
| 41 | 20 | 10 | 0 | 8.0 | 0/10 | 0/10 | 100% |
| 42 | 20 | 10 | 0 | 8.1 | 0/10 | 0/10 | 100% |
| 43 | 20 | 10 | 0 | 8.1 | 0/10 | 0/10 | 100% |
| 44 | 20 | 10 | 0 | 8.0 | 0/10 | 0/10 | 100% |
| 45 | 20 | 10 | 0 | 8.2 | 0/10 | 0/10 | 100% |
| 46 | 20 | 10 | 0 | 8.1 | 0/10 | 0/10 | 100% |
| 47 | 20 | 10 | 0 | 8.0 | 0/10 | 0/10 | 100% |
| 48 | 20 | 10 | 0 | 0 | 10/10 | 10/10 | 0 |

Note:
the HI antibody is determined as the geometric mean of the immunized chicken antibodies.

The results showed that all of vaccines 4, 9-19 in immunization groups could produce a higher content of Newcastle disease virus antibody and compared with the control group, could provide complete protection against the virulent strain. The results showed that the oil emulsion combined vaccine in which the Newcastle disease virus N7a strain solution was prepared as the antigen, could provide complete protection to chickens.

3. Immunogenic Test of Avian Influenza Virus Part 90 21-day-old SPF chickens were divided into 9 groups, that is to say, 10 chickens per group, the chickens in groups 49-56 were immunized by subcutaneous injection in necks with corresponding vaccines 5, 9, 13, 16-19 prepared in Example 13 at an immune amount of 0.3 ml per chicken, respectively, and the chickens in group 57 were injected with On the 5th day after challenge, cloacal swabs were collected. 5 SPF chicken embryos of 10 to 11 days old were inoculated with the treated cloacal swab samples through the allantoic cavity. After incubating for 5 days, both dead embryos and live embryos should be assayed for agglutination titer of the erythrocyte in the chicken embryo solution. Among each five chicken embryos inoculated with one swab sample, as long as the agglutination titer of one chicken embryo solution was not less than 1:16 (micro-method), it can be determined as being positive virus isolation. The samples showing negative virus isolation should be re-determined after one blind passage. There should be at least 9 chickens in the immunization group showing negative virus isolation; and there should be at least 4 chickens in the control group showing positive virus isolation. The results are shown in Table 14.

TABLE 14

Result of immunogenicity test of the avian influenza virus part of the combined vaccine of the fowl adenovirus

| Group | Immune dose (ml per chicken) | Number of chickens | HI antibody detection result ($\log_2$) Before immunization | HI antibody detection result ($\log_2$) Day 21 after immunization | Results of challenge isolation rate of virus | Results of challenge Protection rate |
|---|---|---|---|---|---|---|
| 49 | 0.3 | 10 | 0 | 8.5 | 0/10 | 100% |
| 50 | 0.3 | 10 | 0 | 8.6 | 0/10 | 100% |
| 51 | 0.3 | 10 | 0 | 8.6 | 0/10 | 100% |
| 52 | 0.3 | 10 | 0 | 8.7 | 0/10 | 100% |
| 53 | 0.3 | 10 | 0 | 8.8 | 0/10 | 100% |
| 54 | 0.3 | 10 | 0 | 8.5 | 0/10 | 100% |
| 55 | 0.3 | 10 | 0 | 8.7 | 0/10 | 100% |
| 56 | 0.3 | 10 | 0 | 8.6 | 0/10 | 100% |
| 57 | 0.3 | 10 | 0 | 0 | 10/10 | 0 |

Note:
the HI antibody is determined as the geometric mean of the immunized chicken antibodies.

The results showed that vaccines 5, 9, 13, 16-19 in the immunization groups could produce a higher content of avian influenza virus antibody on Day 21 after immunization and compared with the control group, could provide complete protection against the virulent strain. The results showed that the oil emulsion combined vaccine in which the H9 subtype of avian influenza virus solution was prepared as the antigen, could provide complete protection to chickens.

4. Immunogenicity Test of Avian Infectious Bronchitis Virus Part 80 21-day-old SPF chickens were divided into 8 groups, that is to say, 10 chickens per group, the chickens in groups 58-64 were immunized by eye-drop and norse-drop inoculation with live vaccines (H120 strain) of avian infectious bronchitis virus at an immune amount of 0.05 ml per chickens, respectively. On the 21st day after immunization, the blood samples of the immunized chickens in groups 58-64 together with that of the control chickens in the 65th group were collected, and the corresponding serum samples were separated. Meanwhile, the chickens in groups 58-64 were immunized by subcutaneous injection in necks with corresponding vaccines 6, 10, 13, 14, 15, 18, 19 prepared in Example 13 at an immune amount of 0.3 ml per chicken, respectively. On the 28th day after inoculation, the blood samples of the immunized chickens in groups 58-64 together with that of the control chickens in the 65th group were collected, and the corresponding serum samples were separated. The serum samples collected on the 21th day after first immunization of live vaccines and on the 28th day after immunization of inactivated vaccines were detected for HI antibody titer. For the immunization groups, the geometric mean of the HI antibody titers of the serum samples of second immunization was not less than 4 times of the geometric mean the HI antibody titers of the serum samples of first immunization, and the geometric mean of the HI antibody titers of the non-immunization control group was not higher than 1:8 (micromethod). At the same time, the challenge experiment was conducted with virulent M41 strain of avian infectious bronchitis virus via norse-drop inoculation at $10^{3.0}$ $EID_{50}$ per chicken. The results are shown in Table 15.

TABLE 15

Result of immunogenicity test of the avian infectious bronchitis virus part of the combined vaccine of the fowl adenovirus

| Group | Antibody titer for the first immunization | Antibody titer for the second immunization | Factors of antibody titer for the first immunization versus antibody titer for the second immunization | isolation rate of virus after challenge |
|---|---|---|---|---|
| 58 | 1:18.2 | 1:92.2 | 5.1 | 0/10 |
| 59 | 1:19.6 | 1:101 | 5.2 | 0/10 |
| 60 | 1:21.4 | 1:104.6 | 4.9 | 0/10 |
| 61 | 1:23.8 | 1:121.4 | 5.1 | 0/10 |
| 62 | 1:24.5 | 1:123.8 | 5.1 | 0/10 |
| 63 | 1:23.3 | 1:122.6 | 5.3 | 0/10 |
| 64 | 1:21.8 | 1:125.2 | 5.7 | 0/10 |
| 65 | ≤1:4 | ≤1:4 | — | 5/5 |

The results showed that the geometric means of the HI antibody titers of the serum samples of second immunization for vaccines 6, 10, 13, 14, 15, 18, 19 were not less than 4 times of the geometric means of the HI antibody titers of the serum samples of first immunization, no virus was isolated from all of the tracheas of immunized chickens after challenge. The vaccines 6, 10, 13, 14, 15, 18, 19 could provide complete protection against the virulent strain. The results showed that the oil emulsion combined vaccine in which the avian infectious bronchitis virus solution was prepared as the antigen, could provide complete protection to chickens.

5. Immunogenic Test of the Infectious Bursal Disease Virus Part 60 21-day-old SPF chickens were divided into 6 groups, that is to say, 10 chickens per group, the chickens in groups 66-70 were immunized by subcutaneous injection in necks with corresponding vaccines 7, 11, 14, 16, 18 prepared in Example 13 at an immune amount of 0.3 ml per chicken, respectively, and the chickens in group 71 were injected with 0.3 ml of physiological saline solution by subcutaneous injection, as a blank control. All experimental chickens were fed in isolation. On the 21st day after immunization, the chickens in groups 66-71 were challenged by eye-drop inoculation with 0.1 ml of the virus solution of BC6-85 ((CVCC AV7 strain, purchased from the China Veterinary Drug Administration) of the avian infectious bursal disease virus diluted to 10-2 (actual virus content ≥100BID). After challenge, clinical signs of the chickens were observed daily, and numbers of the incidence, death and rate for protection were recorded. The survived chickens were killed after 72-96 hours, dissections were observed respectively to observe lesions of the Bursa of Fabricus etc. There should be at least 8 normal chickens in the immunization groups showing negative lesions of the Bursa of Fabricus; and there should be at least 4 sick chickens in the control group showing significant lesions of the Bursa of Fabricus (e.g. one or more of lesions such as strip-like bleeding of breast or leg muscle, enlargement or shrinking of bursa of Fabricius, yellowing of bursa of Fabricius, jelly-like secretions within bursa of Fabricius). The results are shown in Table 16.

TABLE 16

Result of immunogenicity test of the infectious bursal disease virus part of the combined vaccine of the fowl adenovirus

| Group | Immune dose (ml per chicken) | Number of chickens | Number of incidence | Protection rate |
|---|---|---|---|---|
| 66 | 0.3 | 10 | 0/10 | 100% |
| 67 | 0.3 | 10 | 0/10 | 100% |
| 68 | 0.3 | 10 | 0/10 | 100% |
| 69 | 0.3 | 10 | 0/10 | 100% |
| 70 | 0.3 | 10 | 0/10 | 100% |
| 71 | 0.3 | 10 | 10/10 | 0 |

The results showed that vaccines 7, 11, 14, 16, 18 could provide complete protection against the virulent strain of the avian infectious bursal disease virus on Day 21 after immunization.

6. Immunogenic Test of the Egg Drop Syndrome Virus Part 60 21-day-old SPF chickens were divided into 6 groups, that is to say, 10 chickens per group, the chickens in groups 72-76 were immunized by subcutaneous injection in necks with corresponding vaccines 8, 12, 15, 17, 19 prepared in Example 13 at an immune amount of 0.3 ml per chicken, respectively, and the chickens in group 77 were injected with 0.3 ml of physiological saline solution by subcutaneous injection, as a blank control. All the experimental chickens were fed in isolation. On the 21st day after immunization, the blood samples of the chickens in groups 72-77 were collected. HI antibody titers of the Egg Drop Syndrome virus were detected, the geometric average titers of the HI antibodies of the immunized chickens should be ≥7 log 2, the geometric average titers of the HI antibodies of the control chickens should be ≤2 log 2. The results are shown in Table 17.

TABLE 17

Result of immunogenicity test of the Egg Drop Syndrom virus part of the combined vaccine of the fowl adenovirus

| | Immune dose | | HI antibody detection result ($\log_2$) | |
|---|---|---|---|---|
| Group | (ml per chicken) | Number of chickens | Before immunization | Day 21 after immunization |
| 72 | 0.3 | 10 | 0 | 7.8 |
| 73 | 0.3 | 10 | 0 | 7.6 |
| 74 | 0.3 | 10 | 0 | 7.9 |
| 75 | 0.3 | 10 | 0 | 7.6 |
| 76 | 0.3 | 10 | 0 | 7.5 |
| 77 | 0.3 | 10 | 0 | All ≤2 |

Note:
the HI antibody is determined as the geometric mean of the immunized chicken antibodies.

The results showed that Vaccines 8, 12, 15, 17, 19 could all produce a higher content of antibody of the egg drop syndrome virus on Day 21 after immunization, which could effectively prevent occurrence of the egg drop syndrome for the chickens. It is proved that the combined vaccine of fowl adenovirus provided by the disclosure could resist the invasion of related pathogens, showing good immunogenicity, and could effectively control the epidemic of the diseases associated with fowl adenoviruses in China.

Example 15 Efficient Expression of Fowl Adenovirus Fiber-2 Protein

The gene fragment of the fowl adenovirus Fiber-2 Protein was obtained through PCR amplification with primers Fiber-F1 (SEQ ID NO. 7): 5-CGCCATATGAGCCTCG-GAAGACTCCGAGCCCCTAAAAG-3, and Fiber-R1 (SEQ ID NO. 8): 5-CCCAAGCTTTTACGGGACGGAG-GCTGCTGGA-3 designed based on the gene of the fowl adenovirus Fiber-2 protein.

The PCR product was sent to Invitrogen Corporation for sequencing, and the sequencing result is as shown in the sequence of SEQ ID NO. 2.

The PCR product was electrophoresed to recover the target fragment and ligated into pET24a plasmid. The linked plasmid was transformed into E. coli BL21 (DE3). The single clone was picked up and cultured in LB medium containing 100 μg/ml of kanamycin overnight. The plasmid was extracted and sequenced. The positive clone was pET24a_FADV_ Fiber-2 expression strain.

The pET24a_FADV_ Fiber-2/*E. coli* BL21 (DE3) strain was inoculated into LB medium containing 50-100 μg/ml of kanamycin at an inoculum amount of 1% (V/V), and cultured with shaking at 37° C. When OD600=0.4-0.6, the sample was placed at 28° C. for 30 minutes. Isopropyl-β-D-1-thiogalactopyranoside (IPTG) was added to a final concentration of 0.1-1.0 mM and the sample was cultured with shaking at 28° C. for 24 hours. After cultivation, the bacteria were harvested and resuspended in PBS (8 g sodium chloride, 0.2 g potassium chloride, 1.44 g disodium hydrogen phosphate, 0.24 g potassium dihydrogen phosphate, adjusted to pH 7.4 with a final volume of 1 L), and the supernatant was obtained by centrifugation after ultrasonic decomposition. The expression product had a higher content of the soluble target protein, the AGP titer of Fiber-2 protein reached 1:128, and the endotoxin had a content of $0.46 \times 10^5$ EU/ml.

Removal of endotoxin was performed according to the method in Example 3. After measurement, the AGP titer of Fiber-2 protein reached 1:128, and the endotoxin had a content of $0.008 \times 10^5$ EU/ml.

The results showed that Triton X-114 could eliminate the residual endotoxin in the recombinant protein and had no effect on the immunogenicity of Fiber-2.

Example 16 Preparation and Immunogenicity Test of Five-Combined Vaccines of Newcastle Disease Virus, Avian Infectious Bronchitis Virus, Avian Influenza Virus, Infectious Bursal Disease Virus and Fowl Adenovirus 1. Preparation of Five-Combined Vaccine The fiber-2 protein purified according to Example 15 was mixed with antigens of Newcastle disease virus prepared according to Example 8, avian influenza virus prepared according to Example 9, avian infectious bronchitis virus prepared according to Example 10, and infectious bursal disease virus prepared according to Example 11 in a certain ratio, respectively, and added to the white oil adjuvant, while the motor was started, stirred at 17500 r/min for 5 min. 1% thimerosal solution was added before termination of stirring to a final concentration of 0.01%. The component ratios are shown in Table 18.

TABLE 18

Component ratios of five-combined vaccine

| Component | Vaccine 20 |
| --- | --- |
| Antigen of N7a strain ($EID_{50}$/0.1 ml) | $10^{8.0}$ |
| Antigen of M41 strain ($EID_{50}$/0.1 ml) | $10^{6.0}$ |
| Antigen of SZ strain ($EID_{50}$/0.1 ml) | $10^{8.0}$ |
| VP2 protein (AGP titer) | 1:16 |
| Fiber-2 protein (AGP tier) | 1:8 |
| White oil adjuvant (v/v %) | 66% |

2. Immunogenic Test of Fowl Adenovirus Part of the Five-Combined Vaccine

The immunogenicity of the fowl adenovirus part of the five-combined vaccine was verified with reference to the method in the immunogenic test of fowl adenovirus part in Example 1 Part 1, group 78 was an immunized group and group 79 was a blank control. The results are shown in Table 19.

TABLE 19

Result of immunogenic test of fowl adenovirus part of the five-combined vaccine

| | Immune dose | | Results of challenge | | |
| --- | --- | --- | --- | --- | --- |
| Group | (ml per chicken) | Number of chickens | Number of incidence | Number of deaths | Protection rate |
| 78 | 0.3 | 10 | 0/10 | 0/10 | 100% |
| 79 | 0.3 | 10 | 10/10 | 10/10 | 0 |

The results showed that immunization groups could produce good immune protection on Day 21 after immunization. The results showed that the five-combined vaccine in which the fowl adenovirus Fiber-2 protein was prepared as the antigen, can provide complete protection to chickens.

3. Immunogenic Test of the Newcastle Disease Virus Part of the Five-Combined Vaccine The immunogenicity of the Newcastle disease virus part of the five-combined vaccine was verified with reference to the method in the immunogenic test of fowl adenovirus part in Example 2 Part 2, group 80 was an immunized group and group 81 was a blank control. The results are shown in Table 20.

TABLE 20

Result of immunogenic test of the Newcastle disease virus part of the five-combined vaccine

| | Immune dose (ml per chicken) | Number of chickens | HI antibody detection result ($\log_2$) | | Results of challenge | | |
| --- | --- | --- | --- | --- | --- | --- | --- |
| Group | | | Before immunization | Day 21 after immunization | Number of incidence | Number of deaths | Protection rate |
| 80 | 20 | 10 | 0 | 8.2 | 0/10 | 0/10 | 100% |
| 81 | 20 | 10 | 0 | 0 | 10/10 | 10/10 | 0 |

Note:
the HI antibody is determined as the geometric mean of the immunized chicken antibodies.

The results showed that all of vaccines in immunization groups could produce a higher content of Newcastle disease virus antibody, and compared with the control group, could provide complete protection against the virulent strain. The results showed that the combined vaccine in which the Newcastle disease virus N7a strain solution was prepared as the antigen, could provide complete protection to chickens.

4. Immunogenic Test of Avian Influenza Virus Part of the Five-Combined Vaccine

The immunogenicity of the avian influenza virus part of the five-combined vaccine was verified with reference to the method in the immunogenic test of avian influenza virus part in Example 14 Part 3, group 82 was an immunized group and group 83 was a blank control. The results are shown in Table 21.

TABLE 21

Result of immunogenic test of the avian influenza virus part of the five-combined vaccine

| Group | Immune dose (ml per chicken) | Number of chickens | HI antibody detection result ($log_2$) Before immunization | HI antibody detection result ($log_2$) Day 21 after immunization | Results of challenge isolation rate of virus | Results of challenge Protection rate |
|---|---|---|---|---|---|---|
| 82 | 0.3 | 10 | 0 | 8.8 | 0/10 | 100% |
| 83 | 0.3 | 10 | 0 | 0 | 10/10 | 0 |

Note:
the HI antibody is determined as the geometric mean of the immunized chicken antibodies.

The results showed that vaccine 20 in immunization groups could produce a higher content of avian influenza virus antibody on Day 21 after immunization, and compared with the control group, could provide complete protection against the virulent strain. The results showed that the five-combined vaccine in which the H9 subtype of avian influenza virus solution was prepared as the antigen, could provide complete protection to chickens.

5. Immunogenicity Test of Avian Infectious Bronchitis Virus Part of the Five-Combined Vaccine The immunogenicity of the avian infectious bronchitis virus part of the five-combined vaccine was verified with reference to the method in the immunogenic test of avian infectious bronchitis virus part in Example 14 Part 4, group 84 was an immunized group and group 85 was a blank control. The results are shown in Table 22.

TABLE 22

Immunogenicity test of avion infectious bronchitis virus part of the five-combined vaccine

| Group | Antibody titer for the first immunization | Antibody titer for the second immunization | Factors of antibody titers for the first immunization versus antibody titers for the second immunization | isolation rate of virus after challenge |
|---|---|---|---|---|
| 84 | 1:21.4 | 1:124.2 | 5.8 | 0/10 |
| 85 | ≤1:4 | ≤1:4 | — | 5/5 |

The results showed that the geometric means of the HI antibody titers in the serum samples of second immunization for vaccine 20 were not less than 4 times of the geometric means of the HI antibody titers in the serum samples of first immunization, no virus was isolated from all of the tracheas of immunized chickens after challenge. The vaccine 20 could provide complete protection against the virulent strain. The results showed that the five-combined vaccine, in which the avian infectious bronchitis virus solution was prepared as the antigen, could provide complete protection to chickens.

6. Immunogenic Test of Infectious Bursal Disease Virus Part of the Five-Combined Vaccine The immunogenicity of the infectious bursal disease virus part of the five-combined vaccine was verified with reference to the method in the immunogenic test of infectious bursal disease virus part in Example 14 Part 5, group 86 was an immunized group and group 87 was a blank control. The results are shown in Table 23.

TABLE 21

Result of immunogenic test of the infectious bursal disease virus part of the five-combined vaccine

| Group | Immune dose (ml per chicken) | Number of chickens | Results of challenge Number of incidence | Results of challenge Protection rate |
|---|---|---|---|---|
| 86 | 0.3 | 10 | 0/10 | 100% |
| 87 | 0.3 | 10 | 10/10 | 0 |

The results showed that vaccine 20 could produce complete protection against virulent infectious bursal disease virus on Day 21 after immunization. The results showed that the five-combined vaccine, in which the avian infectious bursal disease virus VP2 protein was prepared as the antigen, could provide complete protection to chickens.

The foregoing descriptions are merely preferred examples of the present disclosure and are not intended to limit the present disclosure in any form. Although the present disclosure has been disclosed by way of preferred examples, it is to be understood that the disclosure is not limited thereto. A person skilled in the art may make some equivalent variations or modifications to the above-disclosed technical content without departing from the scope of the technical solutions of the present disclosure to obtain equivalent examples. An example present disclosurey simple modifications, equivalent changes and modifications made to the above examples according to the technical essence of the present disclosure all fall within the scope of the technical solutions of the present disclosure without departing from the contents of the technical solutions of the present disclosure.

The invention claimed is:

1. A vaccine composition, wherein the vaccine composition comprises an immune amount of fowl adenovirus Fiber-2 protein or an immune amount of a live vector recombined with gene of the fowl adenovirus Fiber-2 protein, and an adjuvant wherein said fowl adenovirus Fiber-2 protein is protein encoded by a nucleotide sequence shown in SEQ ID NO.1 or SEQ ID NO.2.

2. The vaccine composition according to claim 1, wherein antibody titers to said fowl adenovirus Fiber-2 protein detected by agar gel precipitation test are equal to or greater than 1:2.

3. The vaccine composition according to claim 1, wherein antibody titers to the fowl adenovirus Fiber-2 protein detected by agar gel precipitation test are between 1:2 and 1:16.

4. The vaccine composition according to claim 1, wherein the adjuvant comprises one or more of (1) Alhydrogel® adjuvant, saponins, Avridine, dimethyldioctadecylammonium bromide; (2) water-in-oil emulsion, oil-in-water emulsion, water-in-oil-in-water emulsion; or (3) the polymers of acrylic or methacylic acid, the copolymers of maleic anhydride and alkenyl derivative; and the Ribi adjuvant system, Block co-polymer, Syntex adjuvant formulation, monophosphoryl lipid A, lipid-amine adjuvant, heat-labile enterotoxin from *E. coli*, cholera toxin, Montanide IMS 1314®, muramyl dipeptide and Gel adjuvant.

5. The vaccine composition according to claim 4, wherein the adjuvant is a white oil adjuvant for preparation of water-in-oil emulsion.

6. The vaccine composition according to claim 4, wherein the concentration of the adjuvant ranges from 5% to 70% V/V.

7. The vaccine composition according to claim 6, wherein the concentration of the adjuvant ranges from 30% to 70% V/V.

8. The vaccine composition according to claim 7, wherein the concentration of the adjuvant is 66% V/V.

9. The vaccine composition according to claim 1, wherein the vaccine composition further comprises one or more other antigens comprising antigen of Newcastle disease virus, antigen of avian influenza virus, antigen of avian infectious bronchitis virus, antigen of infectious bursal disease virus, antigen of egg drop syndrome virus, antigen of avian reovirus, antigen of *Escherichia coli*, antigen of *avibacterium paragallinarum*, antigen of *Mycoplasma Synoviae*, antigen of *Mycoplasma gallisepticum*, antigen of *Pasteurella mul-*

*tocida*, antigen of Marek's disease virus, antigen of avian encephalomyelitis virus and antigen of infectious laryngotracheitis virus.

10. The vaccine composition according to claim 9, wherein the other antigens comprises inactivated antigen of Newcastle disease virus, inactivated antigen of avian influenza virus, VP2 protein of avian infectious bronchitis virus antigen, inactivated antigen of infectious bursal disease virus, and inactivated antigen of egg drop syndrome virus.

11. The vaccine composition according to claim 10, wherein the antigens of Newcastle disease virus are inactivated antigens of N7a strain, the antigens of avian influenza virus are inactivated antigens of SZ strain, the antigens of avian infectious bronchitis virus are inactivated antigens of M41 strain, the antigens of infectious bursal disease virus are inactivated antigens of VP2 protein and the antigens of egg drop syndrome virus are inactivated antigens of AV-127 strain.

12. The vaccine composition according to claim 10, wherein antibody titers to the Fiber-2 protein of the fowl adenovirus detected by agar gel precipitation test are between 1:2 and 1:16, the content of the antigens of the Newcastle disease virus is $10^{8.0}$-$10^{9.0}$ $EID_{50}$/0.1 ml before inactivation, the content of the avian influenza virus is $10^{6.5}$-$10^{8.5}$ $EID_{50}$/0.1 ml before inactivation, the content of the avian infectious bronchitis virus is $10^{6.0}$-$10^{7.0}$ $EID_{50}$/0.1 ml before inactivation, and antibody titers to the VP2 protein of the avian infectious bursal disease virus detected by agar gel precipitation test are between 1:16 and 1:128, and the content of the antigens of egg drop syndrome antigen is $10^{7.0}$-$10^{8.0}$ $EID_{50}$/0.1 ml before inactivation.

13. The vaccine composition according to claim 10, wherein antibody titers to the Fiber-2 protein of the fowl adenovirus detected by agar gel precipitation test are between 1:2 and 1:16, the content of the antigens of the Newcastle disease virus is $10^{8.0}$ $EID_{50}$/0.1 ml before inactivation, the content of the avian influenza virus is $10^{8.0}$ $EID_{50}$/0.1 ml before inactivation, the content of the avian infectious bronchitis virus is $10^{6.0}$ $EID_{50}$/0.1 ml before inactivation, and antibody titers to the VP2 protein of the avian infectious bursal disease virus detected by agar gel precipitation test are has an AGP titer of 1:16, and the content of the antigens of egg drop syndrome virus antigen is $10^{7.0}$ $EID_{50}$/0.1 ml before inactivation.

14. A preparation method of the vaccine composition according to claim 1, the preparation method comprises:
(1) cloning a gene of the fowl adenovirus Fiber-2 protein of the present disclosure; (2) transforming and recombining the gene of the fowl adenovirus protein cloned in the step (1) in order to obtain *E Coli* recombined with Fiber-2 protein; (3) expressing the recombinant fowl adenovirus Fiber-2 protein; (4) isolating and purifying the recombinant fowl adenovirus Fiber-2 protein, and treating the purified recombinant fowl adenovirus Fiber-2 protein with a non-ionic surfactant; and (5) mixing the fowl adenovirus Fiber-2 protein with an adjuvant and emulsifying the resulting mixture.

15. A method of preventing and/or treating infection of fowl adenovirus by applying the vaccine composition according to claim 1.

* * * * *